(12) United States Patent
Blischak

(10) Patent No.: US 7,569,049 B1
(45) Date of Patent: Aug. 4, 2009

(54) MULTI-STABLE VALVES FOR MEDICAL APPLICATIONS AND METHODS FOR USE THEREOF

(75) Inventor: Brian Blischak, Allen, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 254 days.

(21) Appl. No.: 10/756,673

(22) Filed: Jan. 13, 2004

Related U.S. Application Data

(60) Provisional application No. 60/439,909, filed on Jan. 14, 2003, provisional application No. 60/439,780, filed on Jan. 13, 2003.

(51) Int. Cl.
*A61K 9/22* (2006.01)
(52) U.S. Cl. .............................. 604/890.1; 251/129.01
(58) Field of Classification Search .............. 604/890.1, 604/892.1, 6.11, 67, 123, 151–154, 9, 33, 604/99.02, 247, 249, 167.01, 167.03, 891.1; 251/129.06, 95, 89, 129.01
See application file for complete search history.

(56) References Cited

U.S. PATENT DOCUMENTS

| | | | | |
|---|---|---|---|---|
| 4,221,219 A | * | 9/1980 | Tucker | 604/141 |
| 4,541,429 A | * | 9/1985 | Prosl et al. | 604/249 |
| 5,273,014 A | * | 12/1993 | Mitobe et al. | 123/336 |
| 5,417,235 A | * | 5/1995 | Wise et al. | 137/1 |
| 6,048,328 A | | 4/2000 | Haller et al. | |
| 6,068,751 A | * | 5/2000 | Neukermans | 204/601 |
| 6,488,652 B1 | * | 12/2002 | Weijand et al. | 604/93.01 |
| 6,520,936 B1 | | 2/2003 | Mann | |
| 6,554,822 B1 | | 4/2003 | Holschneider et al. | |
| 6,589,205 B1 | | 7/2003 | Meadows | |
| 2002/0072733 A1 | * | 6/2002 | Flaherty | 604/890.1 |

* cited by examiner

*Primary Examiner*—Nicholas D Lucchesi
*Assistant Examiner*—Christopher D Koharski
(74) *Attorney, Agent, or Firm*—Christopher S. L. Crawford; Peter Lando; Melissa Acosta

(57) ABSTRACT

The invention relates to multi-stable valves and methods for their use. The multi-stable valves may include a movable physical stop and a position arm. The physical stop may be placed in the path of the arm effectively locking the valve in at least one position upon deactivation of the valve's motivating forces. The valve may be, for example, a micro valve or a microelectromechanical device. Such a valve may be used in implantable drug infusion applications and other applications having limitations on available energy. In one exemplary embodiment, the valve comprises a membrane separating two channels. The membrane may be lifted by activation of a piezo material, opening the channels for fluid flow. A physical stop may be moved into place and the piezo material deactivated, bringing to rest the arm on the physical stop. In this manner, the valve is stabilized in the open position without requiring continuous supply of energy.

7 Claims, 4 Drawing Sheets

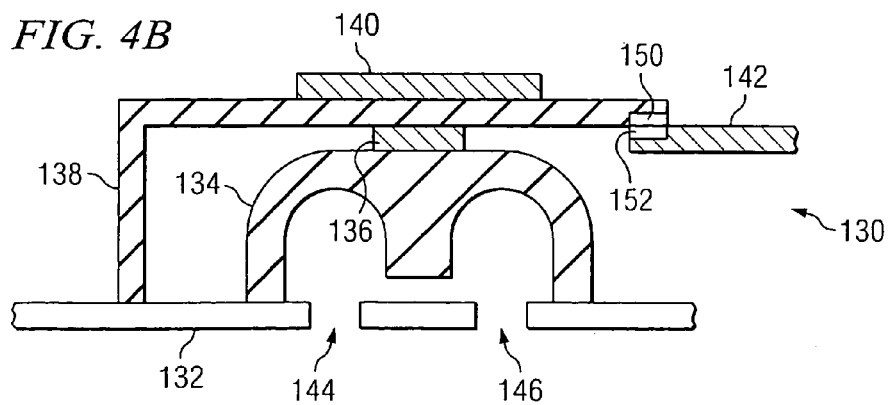
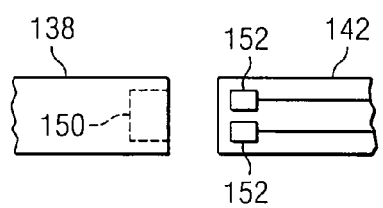
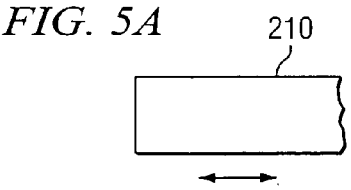
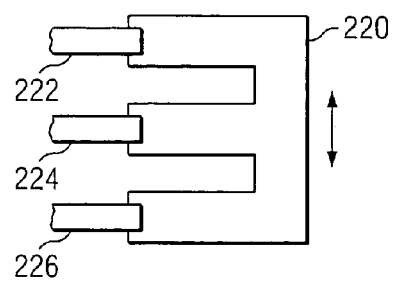
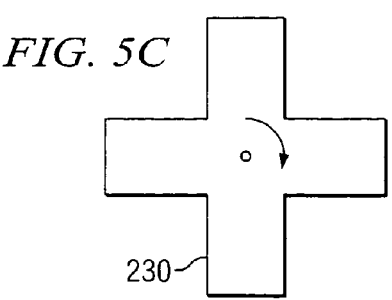
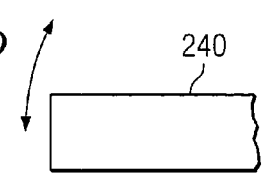

MULTI-STABLE VALVES FOR MEDICAL APPLICATIONS AND METHODS FOR USE THEREOF

CROSS-REFERENCE TO RELATED APPLICATIONS

Priority is hereby claimed to U.S. Provisional Application No. 60/439,909, filed Jan. 14, 2003 and U.S. Provisional Application No. 60/439,780, filed Jan. 13, 2003, the disclosures of which are hereby incorporated herein by reference. The present application is related to the co-pending and commonly assigned U.S. patent application Ser. No. [64862/P009US/10314031], titled "Actuation System and Method for an Implantable Infusion Pump," filed concurrently herewith, the disclosure of which is hereby incorporated herein by reference.

TECHNICAL FIELD

This invention, in general, relates to fluid flow systems. More specifically, the invention relates to multi-stable valves and methods for use thereof in controlling dosage rates of a treatment solution in a medical application.

BACKGROUND OF THE INVENTION

Valves are used in a variety of applications, from large-scaled, bulk flow applications to relatively small flow rate applications. More recently, valves have been used in implantable devices for infusion drug treatment. Flow rates for this application usually range from tenths of milliliters per day to a few milliliters per hour.

Typical valves have a default position. The position may fail opened or closed in the event that energy or an actuation force is lost. In a typical fail-closed valve, a pneumatic or electric force is applied to open the valve and keep it open. For example, in a typical solenoid valve that fails closed, a current is applied to a coil, inducing a magnetic force that drives a piston against a spring, opening the valve. To keep the valve open, the current is continuously applied, consuming energy.

In implantable devices, the available energy is limited by the power source. In some cases, the implanted devices may be recharged through radio frequency energy collection. However, the system is still limited by the size of the battery and the frequency of available recharging. As such, a valve that requires continuous power to maintain a desired position draws down the available power, usually requiring more frequent recharging or battery replacement.

In addition, the continuous use of energy to maintain valve position may cause other problems. Continuous use of sensitive circuitry may cause thermal strain. In various actuation systems, continuous use may lead to leaks, stress on parts, and undesired chemical reactions that adversely affect performance of the valve.

As such, typical valve systems and methods for use may suffer from deficiencies in energy use and use-induced stresses. Many other problems and disadvantages of prior solutions will become apparent to one skilled in the art after comparing such prior solutions with the present invention as described herein.

BRIEF SUMMARY OF THE INVENTION

An embodiment of the invention comprises a multi-stable valve, having physical mechanisms for stabilizing the valve in several positions. In an exemplary embodiment, the valve is a bi-stable valve which can assume two positions, open and closed. In this exemplary embodiment, the valve may be a piezo driven diaphragm valve with a cantilever arm. The cantilever arm operably contacts a physical stop in either the open or closed position. During movement of the valve, the physical stop is moved from the path of the cantilever arm and replaced once the valve is in position. The valve may be actuated by various means including electrostatic, electromagnetic, magnetic torsion, electro-hydrodynamic, electro-osmosis, electrochemical, and mechanical. Furthermore, the valve may use various mechanisms in place of a physical stop, such as a permanent magnet. The valve may be a micro-electromechanical valve. However, various methods may be used to manipulate the cantilever arm and physical stop. The valve may be created on a silicon substrate or other similar materials, or it may be micro-injection molded from tooling created using methods used to construct micro-electromechanical systems.

In an embodiment, a multi-stable valve is employed in a drug infusion application. A system including the multi-stable valve, a treatment solution reservoir, and control circuitry may be used to treat various ailments and conditions.

Other embodiments comprise methods for opening and closing a valve. The method may include moving a physical stop, activating the valve, replacing the physical stop, and deactivating the valve, whereby a valve positioner engages the physical stop. The method may also comprise activating the valve, moving the physical stop, deactivating the valve, and replacing the physical stop.

As such, several embodiments are described. Other aspects, advantages and novel features of the present invention will become apparent from the detailed description of the invention when considered in conjunction with the accompanying drawings.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which:

FIGS. 4A, 4B and 4C are schematic diagrams depicting an exemplary embodiment of a valve system, according to the invention;

FIGS. 5A, 5B, 5C, 5D, 5E and 5F are schematic diagrams depicting exemplary embodiments of a physical stop.

DETAILED DESCRIPTION OF THE INVENTION

Valves are used in various applications from large scale flow to small scale flow applications. In cases in which available energy is limited or in which the size of the valve changes the behaviors and dynamics in the materials associated with the valve's manufacture, continuous application of forces to maintain a valve position may cause unnecessary energy usage and damage to valve parts. One such application is the infusion of drugs and pharmaceuticals through implantable drug infusion systems.

Figure 1:
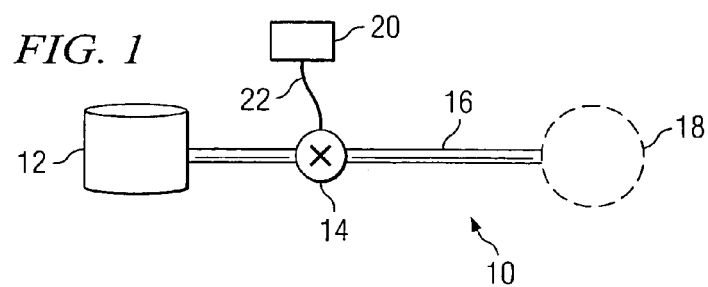
FIG. 1 is a schematic block diagram depicting an exemplary embodiment.

FIG. 1 is a schematic diagram depicting an exemplary embodiment. The system 10 depicts a treatment solution pump and reservoir 12 coupled to a valve 14. Valve 14 controls fluid flow through catheter 16 to treatment location 18. Control circuitry 20 may, through communications link 22, influence the position of valve 14 in accordance with a prescription or desired flow rate. These elements (12, 14, and 20) may be implanted in a patient. As such, power for the operations of these elements is limited by an available battery power or by the frequency of replenishing the power, if available.

In applications such as system 10, the flow rates and thus the sizes of the elements of the valve may be significantly smaller than bulk fluid flow applications. In some embodiments, valve 14 is a micro-electromechanical valve or a micro valve formed on a substrate. A bi-stable valve system may reduce the amount of energy required by valve 14 to produce a desired flow rate because bi-stable valve systems usually only use energy during opening and closing and not in maintaining position. In addition, the stable open and stable closed positions may reduce stresses on those parts associated with the activation of valve 14.

Figure 2A:
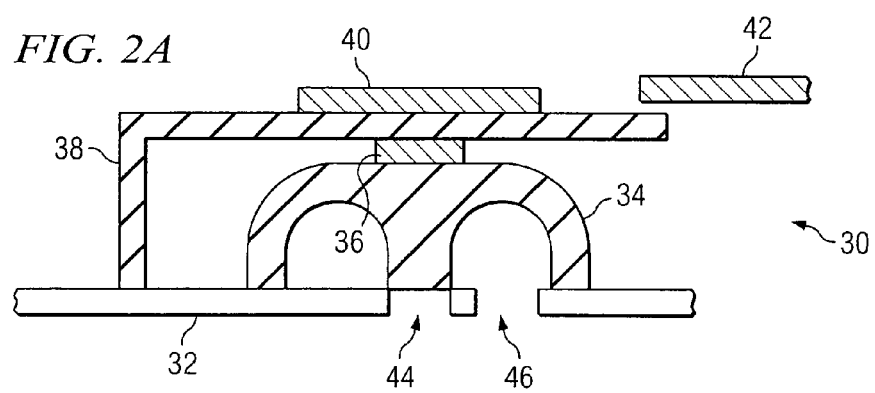
FIGS. 2A, 2B and 2C are schematic diagrams depicting an exemplary embodiment of a valve system, according to the invention.
Figure 2B:
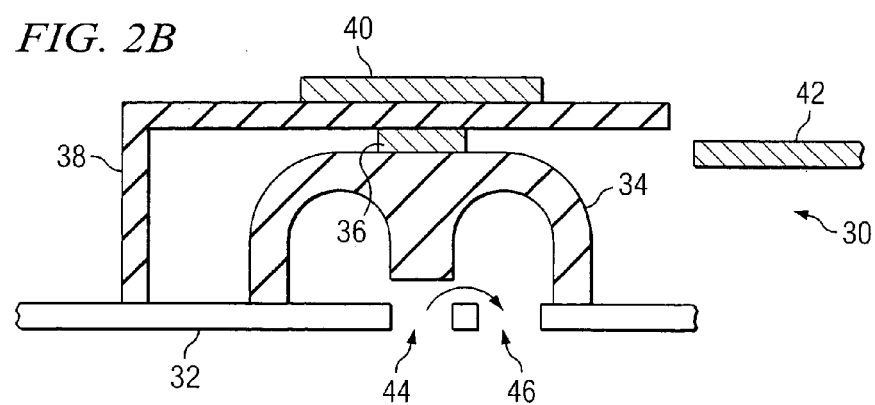
Figure 2C:
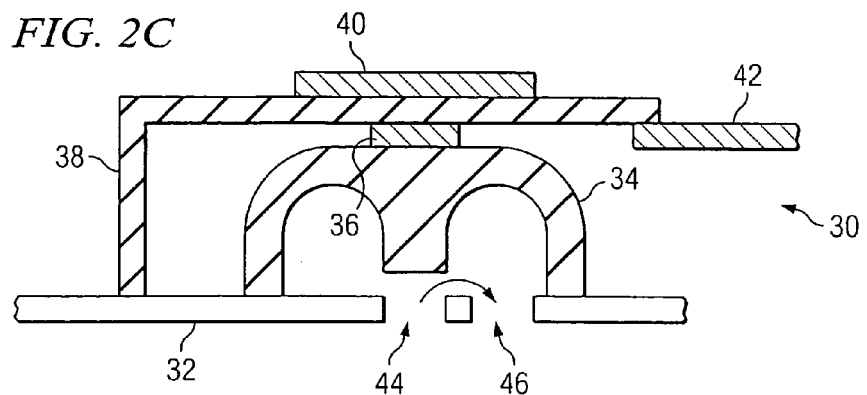

FIGS. 2A, 2B, and 2C depict exemplary embodiments of bi-stable valve system 30. In the illustrated embodiments the valve assembly is formed on substrate 32 having openings 44 and 46. Valve seat 34, incorporated into a diaphragm, acts to block at least one of the openings, here opening 44, in the closed position. Valve seat 34 and the associated diaphragm of the illustrated embodiment are connected to cantilever arm 38 through connecting material 36. Piezo material actuator 40 is coupled to cantilever arm 38. Stop 42 is located in proximity to the distal end of cantilever arm 38 and in the path of cantilever arm 38.

FIG. 2A depicts valve system 30 as closed. Valve seat 34 rests against opening 44, blocking a fluid path between openings 44 and 46. FIG. 2B depicts the opening or activation of valve system 30. Stop 42 is removed from the path of the distal end of cantilever arm 38. Piezo material 40 is activated, and valve seat 34 is moved to allow fluid flow between openings 44 and 46. During this activation, valve system 30 consumes energy through the continued activation of piezo material 40.

FIG. 2C depicts the stable open position of valve system 30. In this figure, stop 42 is moved into place. Cantilever arm 38 rests against stop 42 upon deactivation of piezo material 40. In this manner, fluid may flow through openings 44 and 46 while valve system 30 does not consume energy.

To close valve system 30, piezo material 40 may be reactivated, lifting cantilever 38 from stop 42. Stop 42 may then be removed from the path of cantilever arm 38. Piezo material 40 may be deactivated, lowering cantilever arm 38. Then, stop 42 may be moved back into the path of the distal end of cantilever arm 38.

Although an embodiment incorporating a piezo material actuator, cantilever arm, and stop has been described above, the actuating means associated with a valve assembly of the present invention may take various forms, including, but not limited to, electrostatic, electromagnetic, magnetic torsion, thermal, electro-hydrodynamic, electroosmosis, electrochemical, and mechanical. Further, the valve systems of the present invention may be developed in various size ranges including micro valves and micro-electromechanical devices, among others. According to embodiments, valve assemblies may be manifolded to create a variety of desirable valve options.

Figure 3:
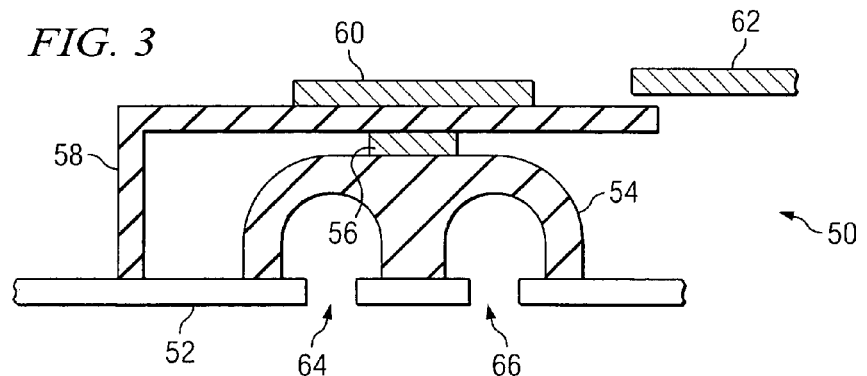
FIG. 3 is a schematic diagram depicting an exemplary embodiment of a valve system according to the invention.

FIG. 3 depicts an alternate embodiment in valve system 50. In this embodiment, substrate 52 has openings 64 and 66. Membrane 54 extends between openings 64 and 66 in a closed position. Membrane 54 is connected through connector 56 to cantilever arm 58. Piezo material 60 is located on cantilever arm 58 in the illustrated embodiment. Physical stop 62 is located in the path of the distal end of cantilever arm 58. Activation of piezo material 60 causes cantilever arm 58 to move upwards bringing membrane divider 54 up and establishing a fluid flow path through openings 64 and 68. In this exemplary embodiment, physical stop 62 may be moved from the path of the distal end of cantilever arm 58 during activation and replaced to stabilize valve system 50 in an open position. Thus, valve system 50 may be placed in an open position without continuous activation of piezo material 60 or continuous use of energy.

Figure 4A:
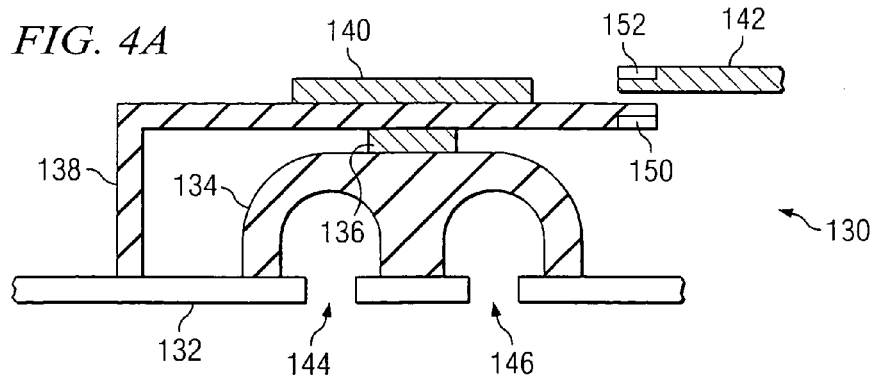

FIGS. 4A, 4B and 4C depict alternate valve embodiments. Valve system 130 of the illustrated embodiment comprises substrate 132 with openings 144 and 146. Membrane 134 separates openings 144 and 146, preventing fluid flow in the closed position. Connector 136 connects membrane 134 to cantilever arm 138. Piezo material 140 is located on cantilever arm 138 of the illustrated embodiment. Physical stop 142 is located in the path of the distal end of the cantilever arm 138. On cantilever arm 138 is conductive material 150. Correspondingly, on physical stop 142 are one or more electrical contacts 152.

As seen in a FIG. 4A, the membrane 134 divides openings 144 and 146, preventing fluid flow. Contacts 152 and conductive material 150 remain out of communication. However, as seen in FIG. 4B, once valve system 130 is open, contacts 152 and conductive material 150 close a circuit.

FIG. 4C depicts one exemplary embodiment of contacts 152 and conductive material 150. When conductive material 150 bridges contacts 152 residing on physical stop 142, a circuit is closed, indicating the position of valve system 130.

However, various sensors and contact configurations may be used to ascertain the state of valve system 130. For example, contacts 152 may be located on cantilever arm 138 and conductive material 150 located on physical stop 142. In an alternate embodiment, one contact may be located on physical stop 142 and an opposite contact located on cantilever arm 138. However, various indicators and sensors may be used to indicate the position of the valve.

Figure 5E:
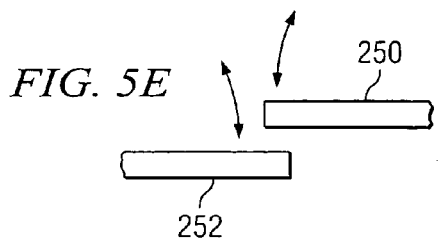

FIGS. 5A, 5B, 5C, 5D, 5E and 5F are schematic diagrams depicting various exemplary embodiments of a physical stop as may be utilized according to the present invention. FIG. 5A depicts physical stop 210 that moves in a horizontal plane relative to a cantilever arm. FIG. 5B also depicts physical stop 220 that moves in a horizontal plane relative to a cantilever arm. Such an assembly as physical stop 220 may also be used as a physical stop for multiple valves. In this exemplary embodiment, cantilever arms 222, 224 and 226 may associated with individual valves. Those valves with cantilever arms resting on the physical stop may be activated. Physical stop 220 moves to the side. Then, valves associated with cantilever arms 222, 224 and, 226 are positioned in their desired states. Cantilever arms 222, 224 and, 226 effectively move between the extensions of physical stop 220. Once the valves are in position, physical stop 220 may be replaced and the valves deactivated, stabilizing them in the desired positions.

FIG. 5C depicts an alternate embodiment in physical stop 230 in which a set of lever arms is rotated to move physical stop 230 in and out of position. In another exemplary embodiment, as seen in FIG. 5D, physical stop arm 240 is motivated in a vertical plane in a sweeping or bending motion. FIG. 5E depicts an alternate embodiment in which physical stop arm 250 is motivated in the vertical plane such that the path of cantilever arm 252 is left clear upon moving physical stop 250.

Figure 5F:
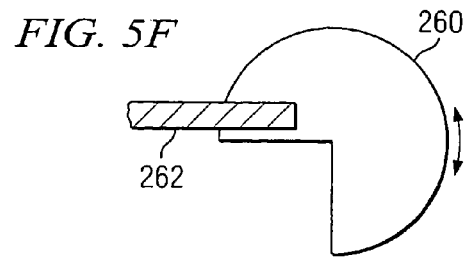

In a further exemplary embodiment as seen in FIG. 5F, physical stop 260 may partially rotate to a position in which the path of cantilever arm 262 is left open. Physical stop 260 is shown as a circle, missing a quarter and can be moved or rotated to a position where the missing quarter is in the path of cantilever arm 262. Once cantilever arm 262 is in the desired position, physical stop 260 may again be rotated into a position in which a physical part of the circle exists.

Figure 6A:
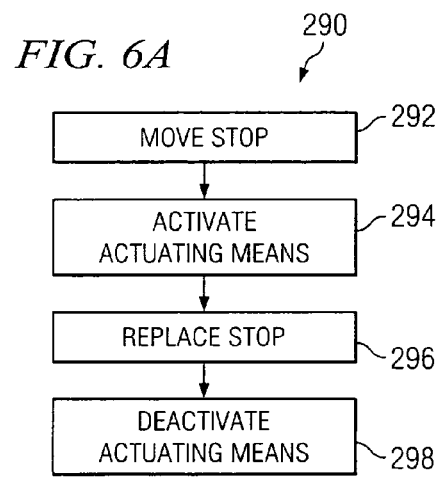
FIGS. 6A and 6B are block flow diagrams depicting exemplary methods for use.
Figure 6B:
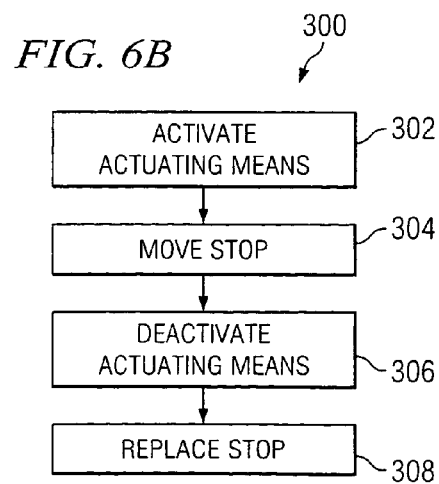

FIGS. 6A and 6B depict exemplary methods. In FIG. 6A, exemplary method 290 includes moving the stop as seen in block 292. As seen in the configurations above, such a method may be used when the valve is in the closed position and the cantilever arm is not touching the physical stop. Next, the valve actuator is activated as seen in block 294. In embodiments, such as those illustrated in FIGS. 2, 3 and 4, piezo material is activated, causing the cantilever arm to move in a vertical direction. The stop can be replaced as seen in block 296. Then, the valve actuator is deactivated as seen in block 298. The deactivation causes the cantilever arm to rest against the physical stop, creating a second stable position for the valve. In this position, the valve does not require the continuous use of energy or cause continuous strain on moving parts. However, an embodiment can be envisioned in which the method 290 of FIG. 6A acts to close the valve.

FIG. 6B is a block flow diagram depicting another exemplary method 300. The valve actuator is activated as seen in block 302. In the examples seen above, activation of piezo material can raise the cantilever arm from the physical stop. The physical stop can then be moved as seen in block 304. Moving the physical stop leaves the path of the distal end of the cantilever arm open, allowing the valve to close on deactivation. The valve actuator is then deactivated as seen in block 306, effectively closing the valve. The stop can be replaced as seen in block 308. However, various embodiments can be envisioned that enable a valve to open with the method 300 of FIG. 6B.

As such, a multi-stable valve and method for operation are described. In view of the above detailed description of the present invention and associated drawings, other modifications and variations will now become apparent to those skilled in the art. It should also be apparent that such other modifications and variations can be effected without departing from the spirit and scope of the present invention.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of operating an implantable drug pump system, the implantable drug pump system comprising (i) a battery for powering the implantable drug pump system, (ii) a valve assembly to control a flow of infusate from the implantable drug pump into the patient's system, (iii) a cantilever arm that is physically coupled to the valve assembly, the cantilever arm being physically adapted to return without consumption of power to a stable first state after application of force to the cantilever arm to move the cantilever arm along a first direction, wherein the cantilever arm comprises first and second opposing longitudinal portions with a distal end of the cantilever arm extending past the valve assembly along a second direction that is generally perpendicular to the first direction, (iv) an actuator for applying force to the cantilever arm to move the cantilever arm along the first direction, and (v) a moveable physical stop that is moveable along the second direction, the method comprising:

(a) moving the physical stop along the second direction to move the physical stop past the distal end of the cantilever arm to permit movement of the cantilever arm along the first direction;

(b) applying power to the actuator to move the cantilever arm along the first direction past the physical stop to cause the valve assembly to change flow states from a first flow state to a second flow state;

(c) moving the physical stop along the second direction to move the physical stop inside the distal end of the cantilever arm after the cantilever is positioned past the physical stop and while power is applied to the actuator;

(d) ceasing to apply power to the actuator to permit the cantilever arm to move along the first direction towards the first stable state;

(e) contacting the distal end of the cantilever arm against the physical stop to prevent the cantilever arm from reaching the first stable state, wherein the contacting causes the cantilever arm to rest against the physical stop in a second stable state without consuming power from the battery and the valve assembly remains in the second flow state.

2. The method of claim 1, wherein the valve assembly is a microelectromechanical valve system.

3. The method of claim 1 wherein the physical stop comprises a plurality of projections to physically stop a plurality of valve assemblies.

4. The method of claim 1 further comprising:
   detecting the state of the valve assembly by determining whether an electrical contact on the distal end of the cantilever arm is in contact with an electrical contact on the physical stop.

5. The method of claim 1, wherein the valve assembly comprises a diaphragm valve.

6. The method of claim 1, wherein the actuator comprises one or more of:
- piezoelectric means;
- electrostatic means;
- electromagnetic means;
- magnetic torsion means;
- electrohydrodynamic means;
- electroosmosis means;
- electrochemical means; and
- mechanical means.

7. The method of claim 1, wherein the valve assembly is implemented on a silicon substrate.

* * * * *

UNITED STATES PATENT AND TRADEMARK OFFICE
CERTIFICATE OF CORRECTION

| | |
|---|---|
| PATENT NO. | : 7,569,049 B1 |
| APPLICATION NO. | : 10/756673 |
| DATED | : August 4, 2009 |
| INVENTOR(S) | : Brian Blischak |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 530 days.

Signed and Sealed this

Seventh Day of September, 2010

David J. Kappos
*Director of the United States Patent and Trademark Office*